United States Patent
Landgraf et al.

(10) Patent No.: US 9,658,168 B2
(45) Date of Patent: May 23, 2017

(54) METHOD AND DEVICE FOR DETERMINING REFLECTION COEFFICIENTS ON FILTER ARRANGEMENTS HAVING THIN LAYERS

(75) Inventors: Johannes Landgraf, Karlsruhe (DE); Günther Proll, Denkendorf (DE); Florian Pröll, Mannheim (DE)

(73) Assignee: Biametrics GmbH, Tuebingen (DE)

( * ) Notice: Subject to any disclaimer, the term of this patent is extended or adjusted under 35 U.S.C. 154(b) by 1050 days.

(21) Appl. No.: 13/318,891

(22) PCT Filed: May 5, 2010

(86) PCT No.: PCT/EP2010/002752
§ 371 (c)(1),
(2), (4) Date: Nov. 4, 2011

(87) PCT Pub. No.: WO2010/127843
PCT Pub. Date: Nov. 11, 2010

(65) Prior Publication Data
US 2012/0058569 A1    Mar. 8, 2012

(30) Foreign Application Priority Data
May 5, 2009  (DE) .................... 10 2009 019 711

(51) Int. Cl.
*G01N 21/77* (2006.01)
*G01N 21/84* (2006.01)
(Continued)

(52) U.S. Cl.
CPC ....... *G01N 21/8422* (2013.01); *G01N 21/253* (2013.01); *G01N 21/77* (2013.01);
(Continued)

(58) Field of Classification Search
CPC .............................. G01N 21/45; G01N 21/21
(Continued)

(56) References Cited

U.S. PATENT DOCUMENTS 5,333,052 A * 7/1994 Finarov .................. 356/369
5,572,598 A * 11/1996 Wihl ................ G01N 21/95607
356/398
(Continued)

FOREIGN PATENT DOCUMENTS

DE    198 06 681 A1    8/1999
DE    198 47 991 A1    4/2000
(Continued)

OTHER PUBLICATIONS

Hans-Martin Schmitt et al.: "An integrated system for optical biomolecular interaction analysis", in: Biosensors & Bioelectronics, vol. 12, No. 8, 1997, pp. 809-816.
(Continued)

*Primary Examiner* — Christopher A Hixson
*Assistant Examiner* — Emily Berkeley
(74) *Attorney, Agent, or Firm* — Muncy, Geissler, Olds & Lowe, P.C.

(57) ABSTRACT

The invention relates to a method for determining optical properties by measuring intensities on a thin layer, wherein light is irradiated onto a carrier (105) that has said thin layer and that is at least partially transparent. Interferences on the at least one thin layer are measured as the relative intensity of at least one superpositioned wave, optionally using filter arrangements (113, 115, 117) provided for this purpose, whereupon the reflection coefficient(s) and/or the transmission coefficient(s) from the reflection and/or the transmission on the thin layer are determined. Preferably, the intensity of at least two superpositioned waves is measured. The light may be irradiated directly onto the carrier. The invention also relates to a device for determining optical properties by measuring intensities on a thin layer, said device comprising an analysis unit which stores at least one lookup
(Continued)

table. The method and the device are preferably used in the area of homeland security.

13 Claims, 6 Drawing Sheets

(51) Int. Cl.
 *G01N 21/25* (2006.01)
 *G01N 21/41* (2006.01)
 *G01N 21/45* (2006.01)
 *G01N 21/23* (2006.01)
(52) U.S. Cl.
 CPC ........ *B01L 2200/148* (2013.01); *G01N 21/23* (2013.01); *G01N 21/41* (2013.01); *G01N 21/45* (2013.01); *Y10S 436/805* (2013.01)
(58) Field of Classification Search
 USPC .................................................. 436/164, 805
 See application file for complete search history.

(56) References Cited

U.S. PATENT DOCUMENTS

| | | | |
|---|---|---|---|
| 5,631,171 A * | 5/1997 | Sandstrom et al. | 436/518 |
| 5,999,262 A * | 12/1999 | Dobschal et al. | 356/504 |
| 6,236,459 B1 * | 5/2001 | Negahdaripour | A61B 3/101 356/496 |
| 2005/0110989 A1 * | 5/2005 | Schermer | G01N 21/253 356/246 |
| 2005/0174584 A1 | 8/2005 | Chalmers et al. | |
| 2007/0051880 A1 * | 3/2007 | Berg et al. | 250/225 |
| 2010/0297671 A1 | 11/2010 | Tschmelak et al. | |
| 2011/0184260 A1 * | 7/2011 | Robinson et al. | 600/316 |

FOREIGN PATENT DOCUMENTS

| | | |
|---|---|---|
| EP | 0 598 341 A1 | 5/1994 |
| WO | WO 97/40366 | 10/1997 |
| WO | WO 2005/028705 | 3/2005 |
| WO | WO 2006/131225 | 12/2006 |
| WO | WO 2008/067528 | 6/2008 |

OTHER PUBLICATIONS

G. Gauglitz et al.: "Chemical and biochemical sensors based on interferometry at thin (multi-)layers", in: Sensors and Actuators B, No. 11 (1993), pp. 21-27.

A. Brecht et al.: "Interferometric measurements used in chemical and biochemical sensors", in: Analusis No. 20 (1992), pp. 135-140.

* cited by examiner

METHOD AND DEVICE FOR DETERMINING REFLECTION COEFFICIENTS ON FILTER ARRANGEMENTS HAVING THIN LAYERS

CROSS-REFERENCES TO RELATED APPLICATIONS

This application is the U.S. National Stage of International Application No. PCT/EP2010/002752, filed May 5, 2010, which designated the United States and has been published as International Publication No. WO 2010/127843 and which claims the priority of German Patent Application, Serial No. 10 2009 019 711.7, filed May 5, 2009, pursuant to 35 U.S.C. 119(a)-(d).

BACKGROUND OF THE INVENTION

The invention relates to a method for determining optical properties by measuring intensities on a thin layer as well as preferred applications, in particular in the area of homeland security.

It is known to determine physical, chemical, biochemical or biological processes, such as reactions, binding and agglomeration processes, and other interactions on a thin layer made of an at least partially optical transparent material by changing the optical layer thickness. For this purpose, light with at least one predetermined selected wavelength is incident on the sample to be tested which is bonded to the thin layer. Interference properties are used to determine changes in the optical layer thickness caused, for example, by a reaction of a material to be tested with the suitably pretreated thin layer.

The measurements can be performed by using suitable markers, for example fluorescence markers. The measurements can nowadays also be performed without markers, as well as with temporal and spatial resolution.

As incident light, either a single wavelength or several, spectrally spaced apart and thus individual different wavelengths are incident simultaneously or sequentially incident on the thin layers to be tested and measured.

Changes in the optical thickness are computed from the spectral position of the interference extremes and their mutual spacing. A shift in the interference pattern can be observed. The optical layer thickness can also be determined from the change in the intensity at one or several wavelengths. Conventionally, the suitable optimal wavelengths are selected so as to provide a maximum change in the expected light intensity.

WO 2008/067528 A2 D1 discloses a so-called "imaging system" on a molecular level, based on the principle of interferometry. Analytes in a sample are hereby measured with a measurement setup having a light source and a detector in form of a pixel array detector, PAD, with a plurality of pixels for capturing the image, so that incident light can be captured and reproduced with good spatial resolution. A bio-layer reacts with the analytes to be determined when the sample to be tested is brought into contact with the bio-layer. This bio-layer is anchored on a substrate capable of converting a phase modulation into an intensity modulation, allowing the intensity modulation to be recorded and directly represented by way of the pixel matrix. Furthermore, a reference surface is provided. Initially, the bio-layer is irradiated and the light reflected from the bio-layer is transmitted to the pixel matrix where the sample is imaged. Via a so-called image changing unit, which may be a mirror, light is, on one hand, incident on the bio-layer and, on the other hand, the incident light is transmitted to the reference surface by moving the mirror accordingly. For this purpose, the light reflected from the reference surface is also transmitted and imaged as reference image. The image from the sample and the reference image are then superimposed using a computer evaluation unit. In lieu of the mirror, the bio-layer and the reference layer can also be alternatingly irradiated using a rapidly rotating disk or a polarizing beam splitter.

EP 0 598 341 A1 discloses one or more sensors for measuring gaseous or liquid components. The respective optical sensor has a thin layer which reacts with the particles to be measured. A reflection which is amplified by interference is measured. The basis for the measurement is the change in layer thickness of the thin layer and/or the change of the refractive index. The measured variable is a change of the intensity of the reflected light. When several such sensors are used, they are intended to measure a different chemical compounds.

The conventional methods are very sensitive to intensity variations of the light incident on the thin layer. With this experimental technique, all conventional methods disadvantageously depend appreciably on the intensity. The measurement results obtained with the conventional methods depend directly on the intensity measurements on the region(s) of the thin layer where changes in at least parts of the layer thickness are caused by the interaction with a sample. Because only very small intensity changes need to be measured, the intensity measurement can be distorted by changes in the brightness of the light source. Intensity variations of the incident light therefore have a direct effect on the quality of the measurement result.

It was also disadvantageous with respect to the reference measurements for the brightness of the light source that a uniform intensity distribution could not be achieved at least for those measurements to be performed by using so-called multi-well plates. For example, a large common light source in conjunction with large lenses was used for a conventional multi-well plate with 96 bottoms in order to illuminate the multi-well plate, in particular the 96 bottoms of the multi-well plate. It has also been observed that only the light intensity in the central region of the field illuminated by the light source was adequate. The sensitivity and reliability of these measurement processes are thus inadequate, making their practical application difficult.

The measurement setup for performing such interference measurements includes essentially a light source, which may be a xenon high-pressure lamp or an LED (light emitting diode or luminescence diode), a planar carrier having a specially activated and pretreated surface, on which the changes in the optical layer thickness are to be measured, a detector, and an evaluation device.

In addition to other disclosures, WO-A-2006/131225 describes a conventional technique relating to details in the preparation of the planar carrier for performing interference measurements.

With respect to the detector, WO-A-97/40366 describes an arrangement having a plurality of discrete photoelectric receivers in form of COD elements arranged in a matrix, thus providing a spatially resolved two-dimensional detector arrangement.

All disclosed measurement setups have in common that they cause a major computational complexity for calculating the changes in the layer thicknesses and the underlying concentrations. The computational complexity is associated with a significant computing time which makes evaluation in real-time with a large number of samples to be analyzed simultaneously very complex and potentially technically impossible.

With this background, it was the object of the present invention to provide a measurement device and a method for determining optical properties on thin layers which operate faster and more precisely than possible to date with conventional devices, and which therefore allow automatic measurements and are therefore suitable for routine applications.

SUMMARY OF THE INVENTION

This object is attained by a method for determining optical properties by measuring intensities on a thin layer, wherein light is incident on at least one partially transparent carrier having the thin layer, characterized by measuring interferences on at least one thin layer are as relative intensity of at least one superpositioned wave, optionally by using suitable filter arrangements, and subsequent determination of the reflection or transmission coefficients from the reflection or transmission on the thin layer.

According to the invention, instead of the intensity of the reflected light wave, the relative intensity of the at least one superpositioned wave, and thus the reflection coefficient on the thin layer is determined.

By determining the reflection coefficient as a ratio of the amplitudes of the incident and the reflected light wave, the value obtained in the determination of the layer thickness becomes independent of the incident light intensity.

The ratio of the amplitude of the reflected or transmitted light to the amplitude of the incident light wave can be determined from the corresponding reflection or transmission factors by using the Fresnel formulas, which can in turn be derived from the Maxwell equations. The ratio of reflected power to incident power is important for the reflection coefficient R, whereas the ratio of the transmitted power to incident power is important for the transmission coefficient T. These basic facts are generally known, but not their application for determining optical layer thicknesses.

The intensity of one or at least two superpositioned waves can thus be measured.

With this approach, not only becomes the measurement result independent of an incident light intensity having the greatest possible uniformity, but it also becomes possible to irradiate the carrier, and therefore the surface with the thin layer and with active elements coupled thereto, directly with light from the near field of a light source. The term direct is intended to indicate that the light does not need to be coupled into the beam path in a complicated manner and that complicated collimator arrangements can also be eliminated.

Reactive elements may be, for example, different biomolecules, such as anti-bodies, which then react with the corresponding species of the sample to be tested, which may be for example antigens. Different reactive elements may be provided by using so-called multi-well plates or flat carriers, for example object slides, wherein the reactive elements are applied with the multi-spot method. The optical layer thickness changes when species of the sample to be tested that correspond with the respective reactive elements are deposited.

Fundamentally, when light is incident on each of the aforementioned carriers having the thin layer with the reactive element(s), a superpositioned field is produced from the incident light field which causes interference effects on which the measurement principle is essentially based.

The intensities of both the generated reflected light field as well as of the generated transmitted light field depend on the thickness of the thin layer. Additional factors play also a role, for example the refractive index of the thin layer.

Reactive elements in the context of the present invention may also be nanoparticles of any type, so that the novel measurement method is generally a measurement method on boundary surfaces. The quantity of interest is thus reduced to the distance between the boundary surfaces.

This extension is possible because the dependence of the measurement result from the light intensity is eliminated by forming the quotient.

When light is incident on an at least partially transparent carrier, a light source with a certain light intensity is required. This light intensity is measured as well as the intensity of the at least one reflected or transmitted superpositioned wave from the thin layer disposed on the carrier. When the quotient is formed from these two values, the reflection or transmission coefficient is obtained, as briefly described below, and thus the actually processed measurement signal.

With a different arrangement or multiple arrangement of the reactive elements on the planar carrier or at the bottom of the multi-weld plate, for example in form of defined patterns, a reflection or transmission coefficient can then advantageously be determined for each individual region of the reactive elements, so that a reflection or transmission coefficient can be associated with each region of the reactive elements. By forming the quotient from reflected or transmitted power to the incident power, the effect of the intensity of the incident light and hence of the intensity of the incident light field is eliminated in favor of the only important change of the reflectivity or transmissivity of the superpositioned wave(s). This also eliminates the noise caused by the intensity variations of the light source which adversely affects the quality of the measurements. The resolution is improved by orders of magnitude over that possible to date in the state-of-the-art.

Whereas in the state-of-the-art necessarily the light of one wavelength or also of several individual wavelengths was evaluated, wherein the evaluation for each individual wavelengths needed to be performed separately, it is desirable and preferred according to the invention to illuminated carrier with light having a narrowband wavelength spectrum and to perform the evaluation together.

A significant acceleration of the evaluation of the measurement results becomes possible only by applying of the novel measurement method according to the invention for determining reflection or transmission coefficients. The data required for compensation can now be stored in a calibration table, currently known as so-called lookup tables.

A lookup table in the context of the present invention refers to a data structure that is prepared and stored using a computer medium. With the lookup table, measurement values can be quickly determined and matched using the quotient determination in table form in reflection or transmission. Such lookup tables advantageously provide rapid matching, which is particularly required for routine tests.

Selectively, narrowband light can be incident, for example, via a light emitting diode, or light of a broad wavelength range can be incident and narrowed to a desired narrow wavelength range with filter arrangement.

According to the invention, the measurements are performed in a narrow wavelength range. Wavelengths with both expected intensity maximum as well as with expected intensity minimum are selected for the measurements.

The term narrow wavelength range is defined for the purpose of the present invention by the wavelength range inherent in a narrowband light emitting diode.

Conventional light emitting diodes (LEDs) are known to emit a limited narrow wavelength band, resulting in quasi monochromatic light. The spectral half width for light emitting diodes is typically between 20 and 35 nm. This half width is also used as a tolerance range for the purpose of the present invention.

According to a preferred embodiment, the method according to the invention is performed without markers, meaning that markers, for example fluorescence markers, are not required.

The desired parameters to be determined from the measurements are derived from the change in the detected light intensity. When measurements are performed at at least two wavelengths or in narrow wavelength ranges, wavelengths with both expected intensity maximum as well as intensity minimum may be selected according to the invention. In other words, unlike with the conventional principle of reflectometric interference spectroscopy, measurements are also performed at those wavelengths where actually nothing happens. The parameters to be determined are then obtained from the relative comparison with those wavelengths that produce or at least suggest intensity maxima.

According to a particular embodiment of the method of the invention, the optical properties are measured by measuring intensities on a thin layer that is divided into several partial regions arranged on the at least partially transparent carrier. Such partial regions are known as multi-spots. Light in at least one narrow wavelength range is hereby incident at least on a part of the partial layer regions. These layer partial regions each have at least two boundary surfaces where the wave fields are superimposed, creating a superpositioned field. The interferences on the layer partial regions can thus be measured as relative intensity of at least one respective superpositioned wave and each transmitted to at least one detector. In addition, the intensity of the spatially incident light on at least a portion of these coated partial regions or multi-spots is measured with an intensity sensor associated specifically with this partial region.

The invention also relates to a device for determining optical properties by measuring intensities of a thin layer, with at least one light source emitting light in at least one narrow wavelength range directly adjusted for an at least partially transparent carrier having the thin layer, and wherein the light source irradiates at least a partial region of the thin layer, and with at least one detector cooperating with a reference detector for spatially and/or temporally resolved measurement of light intensities in the at least one irradiated partial region, as well as an evaluation unit in which at least one lookup table is stored.

Unlike with conventional measurement setups for determining optical properties, which include, for example, measurement setups in the field of reflectometric interference spectroscopy (RIfS), the arrangement according to the invention requires neither a collimator arrangement for producing a parallel beam path, nor coupling elements in the measurement beam path for directing the light of the at least narrow wavelength range onto the thin layer. The light is instead directly incident, without coupling prisms or optical coupling fluids of the type used in the state-of-the-art for preventing unwanted reflections.

By irradiating the carrier with the thin layer directly with the light source, the desired reflection is produced, commensurate with the interaction of the species of a sample to be tested with the corresponding coating of the thin layer, wherein unwanted effects can be ignored because relative intensities are measured and processed.

It should be noted in this context that the use of a wedge-shaped carrier plate, as disclosed in WO-A-97/40366 as possible embodiment, can also be viewed in the broadest sense as a coupling element, because it is this element which enables the special design of the carrier plate, so that the otherwise used coupling prism can be eliminated. According to the aforementioned embodiment in the WO-A-97/40366, the carrier operates at the same time as receiving element for the thin layer and as coupling element.

With the device according to the invention, the relative intensity can be measured in a narrow wavelength range and the respective layer thickness of the thin layer which may have changed through interaction with the species of a sample to be tested can be deduced from this relative intensity. It should be noted here that the thin layer specifically prepared for the aforementioned interaction may also be prepared so that it does not interact with the sample to be tested over the entire area, but only in selected partial regions. In addition, defined partial regions of the thin layer may undergo a different sample preparation, thereby allowing an analysis of different species of a sample.

The preparation of a carrier used, for example, in the field of reflectometric interference spectroscopy has been amply described in patents and in the technical literature and is therefore known to a skilled artisan, and reference is made here to the entire contents of the patent and technical literature.

According to an embodiment, a large-area light source, preferably in form of a high-power light emitting diode or a laser diode, can be used and coupled to at least one wavelength filter for selecting a narrowband wavelength range. This allows rapid measurements of spatially recorded intensities.

According to another embodiment, a light source arrangement composed of several light sources may be used, whereby likewise high-power light emitting diodes or laser diodes may be used. This is particularly advantageous when the thin layer is not so uniformly prepared that only one species of the sample can be tested, but regions with different substances are provided in conjunction with a multi-spot application, wherein each individual region (point) is each selectively irradiated by a light source.

In another implementation of this embodiment, the light sources may be combined into a matrix-like structure, wherein each of the light sources is in turn associated with an individual region (spot) of the thin layer. This can be achieved or ensured by using suitable optical shielding elements which are known to a person skilled in the art.

According to another embodiment, a ring or a group of several light sources may be associated with a spot of the thin layer, and the overall arrangement of the light sources may consist of several such rings or groups of light sources, when the thin layer is provided and prepared for analyzing several species in a sample.

The at least one light source is preferably not directly connected with the carrier having the thin layer. In this way, the light source need not be rejected together with the carrier. The same applies to the detector arrangement.

The reflection caused by the employed light source(s) is detected and recorded as intensity, wherein the term "recording" is to be understood in its broadest sense.

According to the invention, the sensor used for such recording can be configured as a one-dimensional or a two-dimensional CCD sensor.

The light sensitivity of such CCD sensors is known. The signal produced by the sensors is directly proportional to the incident light. When using one-dimensional CCD sensors operating as so-called line sensors, these are referred to as COD arrays in the context of the present invention, commensurate with the commonly used technical designation.

When using two-dimensional CCD sensors, these are also referred to as CCD image sensors, commensurate with the commonly used technical designation. According to the invention, two-dimensional CCD sensors constructed as a matrix of light-sensitive photodiodes or pixels are employed. Particularly preferred, CCD image sensors are used which ensure a balanced relationship between light sensitivity and dynamic range of the sensor, defined across its pixel area, and the image resolution which is known to be inversely proportional to the light sensitivity.

The blooming effect and thus the bleeding of charge due to overexposure can be prevented with suitable coupling between light sources and the light sensors. Advantageously, a so-called "anti-blooming gate" can be eliminated, which could result in a nonlinearity between the incident and detected light and the associated signal, depending on the selected exposure times and thus depending on the sample is to be tested.

The same applies mutatis mutandis also for the CCD arrays.

When using CCD image sensors, these are in a preferred embodiment used in form of a two-dimensional camera system producing an optical image of the chemical compounds disposed on or coupled with the thin layer, for example arranged as spots. This camera system is preferably constructed in the aforementioned digital form and essentially completely images the compounds of the thin layer, regardless if arranged across an area or in spots, by way of the pixels.

The use of CCD arrays is always preferred when the reflected light is to be detected in structured form, so that the light incident on the carrier with the thin layer, preferably in form of individual light sources, can be directly associated individually for the respective illuminated individual spot on the thin layer with the respective spot. This is advantageous in particular with different compounds disposed on the thin layer or coupled to the thin layer, enabling selective detection of different components in the sample to be analyzed.

A number of signals can then be recorded, with each signal originating from the individual spots of the thin layer illuminated with the light source(s). An actual pattern recognition is then not required, the amount of data is significantly reduced and the signal quality is thereby improved.

Moreover, the sensor element(s) is/are formed separate from the carrier with the thin layer and preferably arranged adjacent to the light source(s).

It has been observed that a particularly good signal-to-noise ratio can be obtained when a plurality of sensors, selectively constructed as CCD arrays and/or as CCD image sensors, are surrounded by groups of individual light sources, which each selectively irradiate by way of a suitable shielding only one or several spots of the thin layer. In other words, the reflected radiation from the associated spot is selectively directed to the corresponding associated sensor.

The carrier itself can be arbitrarily selected. This relates to the material and the shape, as long as the carrier has at least partially transparent regions used for the analysis, i.e., for determining the intensity. For example, the carrier may be formed as a flat, two-dimensional carrier or a carrier in form of a micro-titer plate. Suitable carriers and carrier materials are sufficiently known to the skilled artisan, for example from the field of reflectometric interference spectroscopy.

In particular, but not exclusively, when the carrier is a micro-titer plate, the device for determining optical properties by measuring intensities can be constructed in a particular embodiment for measurements on a thin layer divided into several partial regions, the so-called multi-spots. To this end, the device according to the invention includes at least one light source emitting light in at least one narrow wavelength range directly adjusted for at least one partially transparent carrier having the so-called layer partial regions. The at least one light source irradiates the respective layer partial region. At least one detector is provided which cooperates with at least one reference detector. Each of these layer partial regions has at least two boundary surfaces where superpositioned wave fields produce a superpositioned field which is transmitted to the at least one detector. At least a portion of the coated partial regions is associated with at least one intensity sensor for determining the intensity of the light spatially incident on the partial region.

The invention also relates to the use of the device for determining optical properties by measuring intensities on a thin layer, as described above, and the likewise aforedescribed method for identifying chemical, biochemical, medical and/or physical reactions, binding and/or agglomeration processes as well as other interactions. Preferably, this application relates to homeland security.

BRIEF DESCRIPTION OF THE DRAWING

The invention will now be described in more detail with reference to exemplary embodiments and the appended drawing.

It is shown in.

DETAILED DESCRIPTION OF PREFERRED EMBODIMENTS

Figure 1:
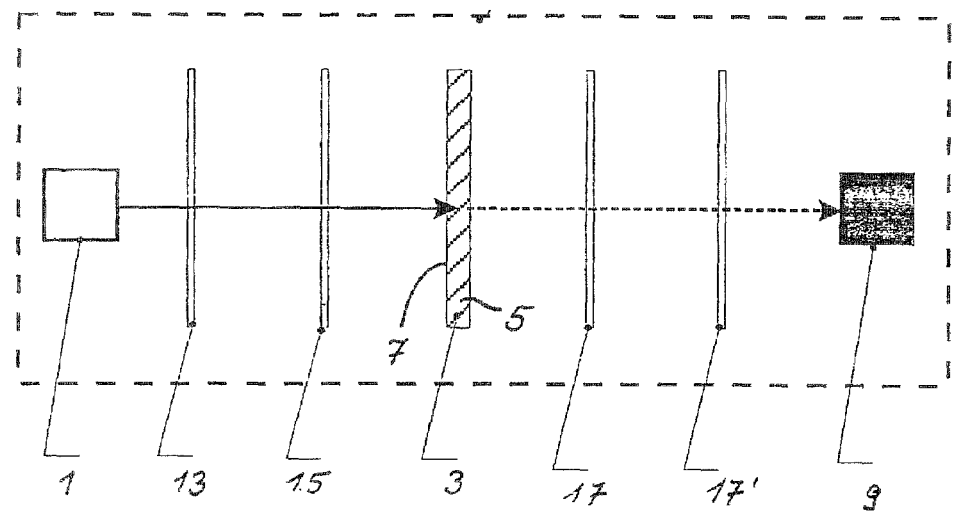
FIG. 1 a schematic diagram of an experimental setup with a two-dimensional carrier and different filters.

The reference symbol 1 in FIG. 1 refers to a light source in form of a high-intensity light emitting diode (LED) capable of emitting light in a narrow wavelength range. The light is transmitted directly to the sample, indicated with the overall reference symbol 3, to be tested without using a coupling element, and also without using a collimator for producing a parallel light beam.

The sample 3 includes an at least partially transparent carrier 5 which in this exemplary embodiment is made of glass in form of an object glass slide and on which a thin layer 7 is applied. For application of this thin layer 13, the designated surface of the carrier 5 is first activated by producing OH-groups on the glass surface.

The glass surface is now prepared for a surface treatment in form of silanization with epoxy groups, which is in this case performed with an epoxy silane in form of 3-(glycidyl oxypropyl) trimethoxy silane (GOPTS), wherein this is only one of many possible compounds for silanization and is only provided as an example. Following the silanization, a reaction with a biopolymer, such as polyethylene glycol (PEG) having a suitable chain length, is performed. However, at least two different PEG with different chain lengths can also be used. Only then are selected specific receptor molecules immobilized with the biopolymer, which completes the preparation of the thin layer for the detection of the desired species in the sample to be investigated.

This formation and preparation of the thin layer 7 for the purpose of the present invention is only briefly summarized, because a person skilled in the art will find more comprehensive information in the state-of-the-art to which reference is made here in full. The present invention is not concerned with the formation of the thin layer 7, but rather with the analytical side of light irradiation, detection and processing of the generated signals.

The thin layer 7 is affected by the sample to be tested, because the interaction of the receptor molecules on the thin layer 7 with the corresponding species in the sample causes a change in the layer thickness in the region of the interaction. This change in layer thickness in turn affects the light that is incident on the carrier 5 and reflected at the surface of the thin layer 7, which is subsequently detected by the detector arrangement 9. The detector arrangement 9 has at least one photodiode and is connected to an unillustrated evaluation unit.

The evaluation unit illustrated in detail below includes essentially a computer system for control, data acquisition and evaluation. The evaluation unit also enables the corresponding association of the reflection with different positions on the carrier 5. This is important for tests with a carrier 5 prepared according to the "multi-spot method", i.e., with specifically prepared regions, the spots, within which the receptor molecules, optionally also different receptor molecules, can be applied. Completely different reactions and interactions can then be tested at the individual spots with the species present in the sample to be tested. In general, this method is suitable for all tests of biomolecular interactions. The tests can also be performed in completely different ways.

It can be determined through the selection of the receptor molecules, if the species present in the sample to be tested interact selectively or non-selectively with the thin layer 7 or only with partial regions (the spots) of the thin layer, thereby causing at least partially a change in the layer thickness.

The spots distributed over the surface of the carrier 5 can be arranged in form of a matrix. In this way, a spatially resolved interaction with the corresponding species of interest in a sample, for example with hormones or antibodies, can be initiated and correspondingly detected and analyzed.

When only specific regions of the surface of the carrier 5 have receptor molecules, specific and non-specific binding effects and therefore interactions can be differentiated by comparing the detection in these regions with untreated regions of the surface of the carrier 5.

Important for the significance of these tests which are possible in many ways is the quality of the obtained data material and its evaluation. For the quality of the evaluation, not only is a good signal-to-noise ratio important but also the ability to apply such tests in a quantitatively meaningful way. This was the object of the invention and will therefore be described in more detail below.

Fundamentally, by irradiating with the light from the light source 1 the thin layer, which as a whole or in defined regions—the spots—interacts through the specific coating with biopolymers and receptor molecules with species of a sample and which thus causes a change in the layer thickness, a corresponding superpositioned field is produced in transmission and another superpositioned field is produced in reflection from the superimposed point waves of the incident light. The reflected superpositioned field is preferably considered for the purpose of the present invention. However, the transmitted superpositioned field may likewise be considered.

The quality of the evaluation can be improved by employing different filters with different functions, as schematically illustrated in FIG. 1. The reference symbol 13 designates a filter used to suitably limit and change the wavelength range, when a broadband light source is employed instead of a light emitting diode. The filters 13 can also be an optical polarization filter for preferably producing linearly polarized light.

When the thin layer is coated with the multi-spot method in specific spaced-apart regions, the spots, where specific interactions with species of the probe(s) to be tested occur, it has proven to be advantageous to employ a spot filter 15, i.e., a point lens. This spot filter 15 is inherently narrowband, and the reflection of the light on the thin layer, i.e., the spots of the thin layer, is measured at the wavelengths selected by the spot filter 15.

In the exemplary embodiment, two detector filters 17, 17', which are also narrowband but do not coincide with the wavelength(s) of the spot filter 15, and which are slightly offset therefrom, are arranged following the carrier 5 with the thin layer 7.

In this way, an overlap range is attained where all three employed filter types 13, 15, 17, 17' are transparent.

Figure 2:
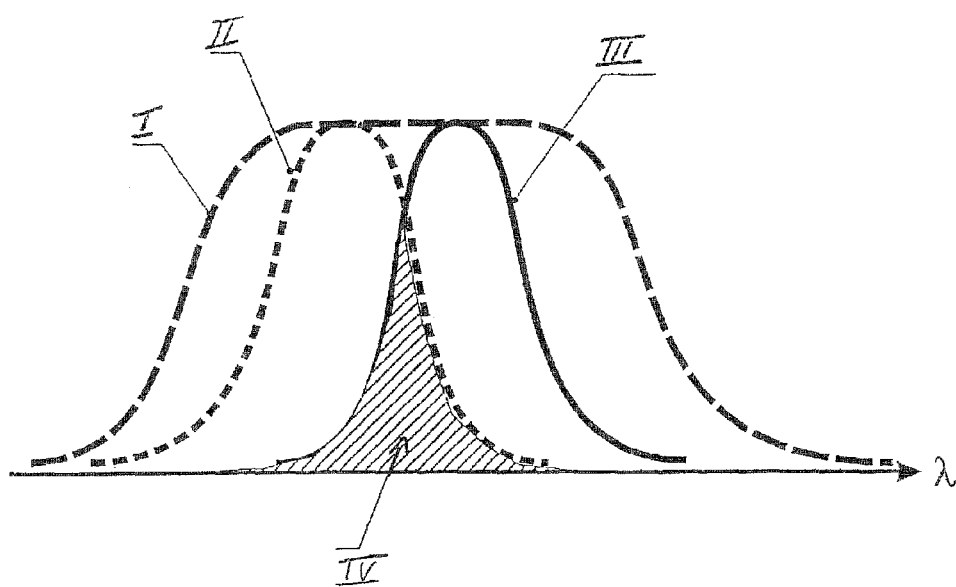
FIG. 2 a wavelength diagram for the experimental setup according to FIG. 1 with filtered ranges and an overlap range.

The resulting wavelength diagram is shown in FIG. 2. The intensity is plotted on the y-axis and the wavelength on the x-axis. The filter 13 determining the wavelength range of the light incident on the carrier 5 is herein shown for a broadband light source 1, meaning that not only a narrowband spectrum is passed. Accordingly, the obtained wavelengths diagram is broadband and illustrated by the continuous line I. The spot filter 15 is narrowband. In this way, the reflection can be measured selectively and wavelength-dependent in a predetermined narrow wavelength range, without having to only select a narrowband light source 1, e.g., a light emitting diode. The corresponding curve is labeled in FIG. 2 with II. The detector filter(s) 17 is/are also selected to be narrowband, with the corresponding overall wavelength range slightly offset from the wavelength range of the spot filter 15. This produces the curve indicated with III.

As seen from FIG. 2, this filter arrangement produces an overlap region IV, with all filters I-III being transparent. With this overlap region IV, the quality of the measurement can be specifically controlled according to the invention depending on the available system to be tested. The broader and larger the overlap region IV is, the larger is also the intensity of the incident light on the detector and the detector arrangement 9, respectively. For example, when the transmission curve II of the spot filter 15 changes while the other two filters I and III remain the same, the light intensity detected by the detector arrangement 9 also changes.

Figure 3:
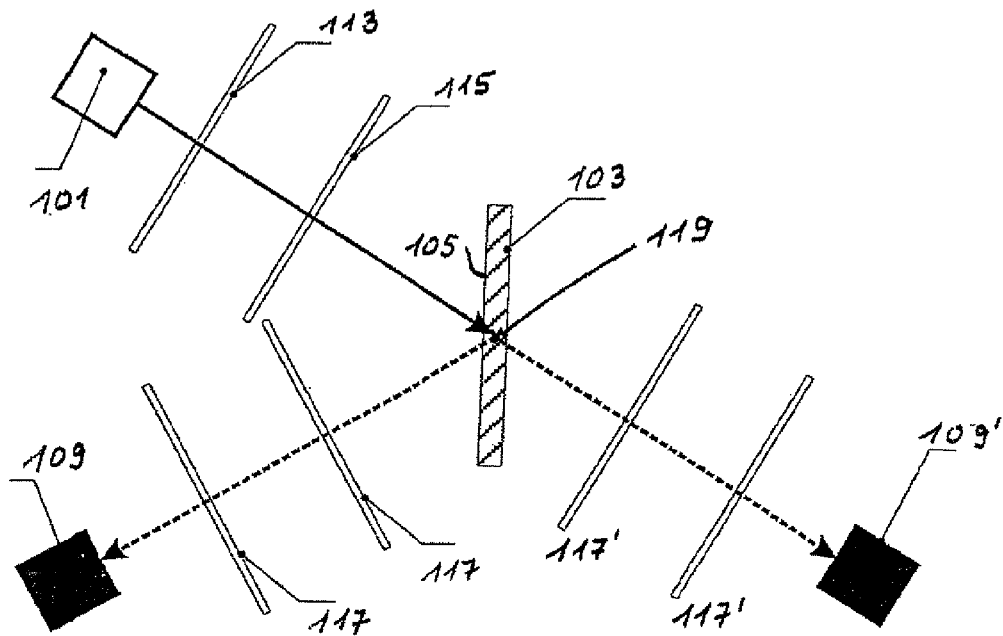
FIG. 3 a schematic diagram of an experimental setup according to the invention with a two-dimensional carrier and a partially reflecting spot.

FIG. 3 shows another embodiment using the same measurement principle. Elements of the measurement setup identical to those of FIG. 1 are indicated with identical reference symbols, augmented by 100.

In FIG. 3, a light source 101 arranged on the left side is again incident on a sample 103, with a carrier 105 having a thin layer 107. A portion of the incident light is reflected by the sample 103 to the detector 109 also located on the left side of the measurement setup. Prior, the incident light passes through the filter described above with reference to the setup in the first embodiment, the wavelength filter 113, the spot filter 115 and the detector filter(s) 117.

The transmitted light propagates in FIG. 3 to the right and is detected by the detector arrangement 109' after passing through the also provided detector filter(s) 117. The reference symbol 119 indicates a likewise provided reference beam path.

It should be noted here that the filter arrangements illustrated in FIGS. 1 and 3 are optional. The described measurement principle can also be implemented by a skilled artisan in other ways, i.e., by replacing at least a part of the aforementioned filters with other measures.

Figure 4:
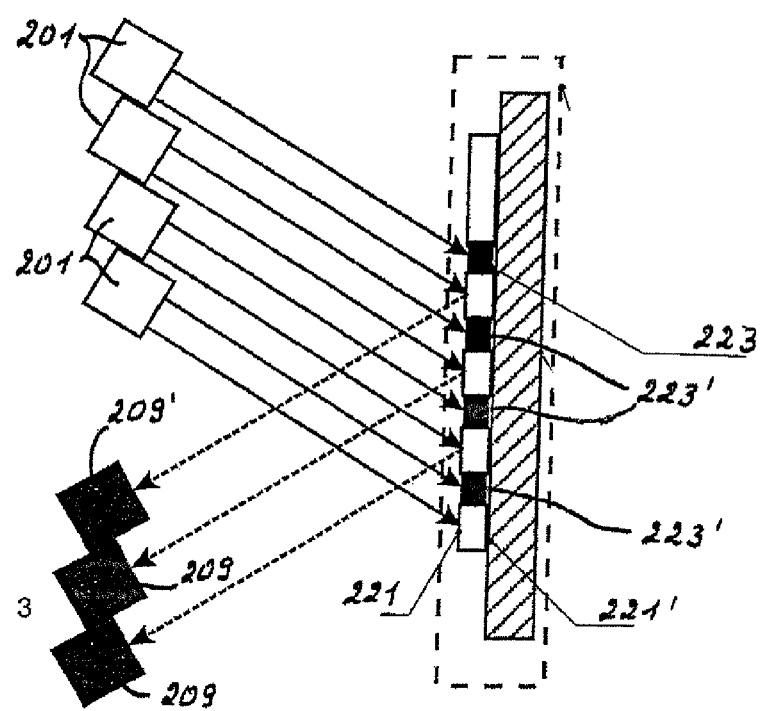
FIG. 4 a schematic diagram of an experimental setup according to the invention with a plurality of light sources and a corresponding plurality of detectors.

This is also shown in FIG. 4 which illustrates another embodiment of the measurement principle according to the invention. Elements of the measurement setup identical to those of FIG. 1 are indicated with identical reference symbols, augmented by 200.

Several light sources 201 are shown in the measurement setup according to FIG. 4, with corresponding detector arrangement 29 associated with the light sources 201; however, one light source, the light source indicated as the first light source in FIG. 4, is associated with a reference detector 209'.

The sample 203 with the carrier 205 does here not have an applied full-surface thin layer 207, but has instead partial regions 207 applied with a multi-spot method with the corresponding biopolymers and receptor molecules attached thereto for interaction with the corresponding species of a sample to be tested.

A respective light source 201 is associated with each of the partial region 207' of the thin layer 207. The partial regions 207' have at least two boundary surfaces 221, 221' where superpositioned wave fields are generated which create the superpositioned field reflected in the direction of the detectors or detector arrangements 209.

According to this exemplary embodiment, local intensity sensors 223, 223' are arranged between the coated partial regions 207' which can be used to determine the incident light at the location of the partial regions 207'.

Such an arrangement does not require the filters used in the previous examples, without having to depart from the principle of measuring the intensity of at least one superpositioned wave with subsequent determination of the reflection and transmission coefficients.

Figure 5:
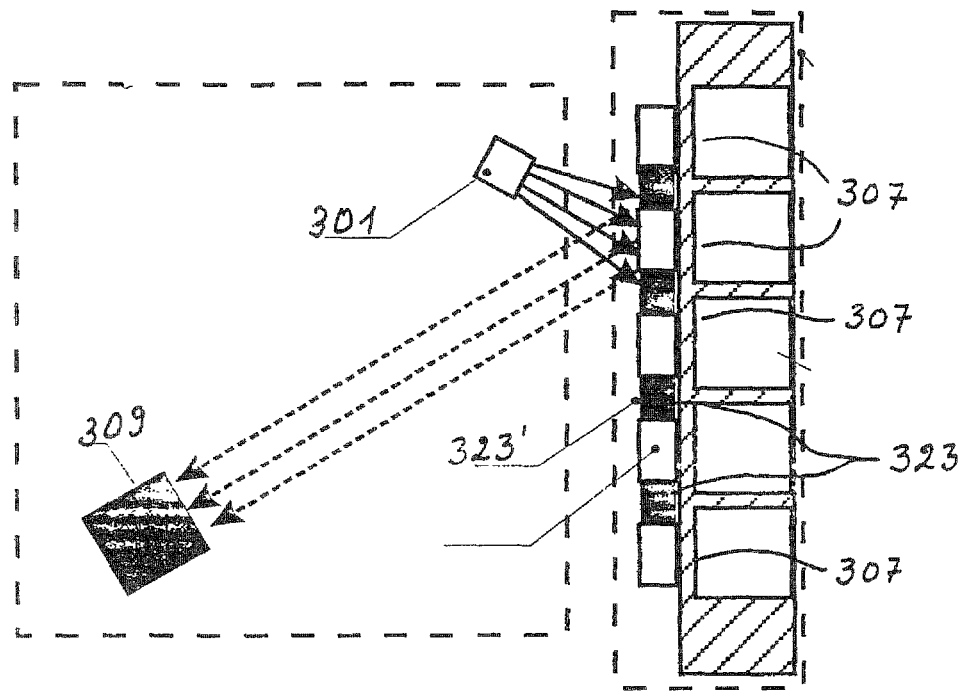
FIG. 5 a schematic diagram of an experimental setup according to the invention with a broadband light source and a corresponding plurality of detectors.

A variation of the arrangement according to FIG. 4 is illustrated in FIG. 5, wherein elements of the measurement setup are again indicated with identical reference symbols, augmented by 300.

A light source 301 is here used for illuminating a group of partial regions 307' of a thin layer 307. Three different variants were tested, not all of which are illustrated in FIG. 5 for sake of clarity and will instead only be described at this point:

1. Variant:

Initially, a light source 301 having a wider surface area is used and is incident simultaneously on the entire group of partial regions 307' of the thin layer 307.

2. Variant:

According to this second variant, a strip-like light source 301, typically an LED light strip, is used to irradiate the group of partial regions 307' of the thin layer 307.

3. Variant:

In this variant, a moving light source 301 scans from one partial region 307' through the next partial regions 307' of the thin layer 307.

All variants 1-3 produce the same acceptable result.

The intensity of the incident light is determined with the intensity sensors 323. The intensity may vary at the different measurement locations on the partial regions 307' of the thin layer 307, without adversely affecting the quality of the measurement result.

In this exemplary embodiment, unlike in the previous embodiments, a multi-well plate is used as carrier 305.

When using the micro-titer plate as carrier 305, the thin layer is applied to its bottoms, also referred to as wells. To apply this thin layer 307, the bottoms of the wells are first activated in the same manner as described above with reference to the carrier surface, by producing OH-groups on the bottoms of the wells. Thereafter, the surface is treated by a silanization with epoxy groups, which is again performed with an epoxy silane in form of 3-(glycidyl oxypropyl) trimethoxy silane (GOPTS). Following the silanization, a reaction is performed with a biopolymer, such as polyethylene glycol (PEG) having a suitable chain length. Again, at least two different PEG having different chain lengths can be used. Only then are selected specific receptor molecules immobilized with the biopolymer, thereby preparing the bottoms of the wells 112 for detection of the desired species in the sample to be tested.

In this briefly described, commonly known preparation of the bottoms of the wells, which is thus far not substantially different from the preparation of the surface of other carriers 305, the activation of the bottoms of the wells and the additional treatment was not performed over the full area, but instead only defined regions of the bottoms of the wells were treated in the aforementioned manner. These defined regions were formed so as to form predetermined, well-defined patterns. The subsequent measurement was therefore used not only to determine the change in the layer thickness due to interaction of the species to be tested in the probe with the thin layer, but was simultaneously also used to recognize the pattern previously applied to the thin layer, which poses significantly higher demands.

Patterns can be imprinted and detected on the surface of the bottoms of the wells in the following regions:

patterns during activation of the bottoms of the wells and/or
patterns during surface treatment in form of a silanization and/or
patterns during the reaction with a biopolymer and/or
patterns during immobilization of the selected specific receptor molecules.

The patterns are either applied by activation or silanization of defined partial regions, or by reaction with the polymer or by immobilizing the receptor molecules in defined partial regions, or by transferring the pattern structure formed in a previous step to the following reaction step.

For example, if only a defined partial region of the surface of the bottoms of the wells was activated at the beginning, then only these activated regions can be silanized. The pattern therefore continues. Likewise, the patterns may be formed only during the conversion step of the silanization by applying a mask, by a specific multi-spot application and the like. The same applies to each of the conversion steps up to the immobilization of the receptor molecules.

The pattern formation described here in a simplified manner is used for coding the respective micro-titer plate or likewise for coding of the respective two-dimensional carrier 305, for example for distinguishing counterfeit products from genuine products and thus providing quality assurance. This pattern formation and coding as such is not part of the present invention. The present invention is directed to capturing and evaluating the formed pattern together with the change in the layer thickness caused by the respective observed interaction in high-quality, preferably automatically.

The light incident from the light source 301 is then detected either directly by the respective intensity sensors 323 or is used in an intensity sensor 323' which captures all the individual intensities. For this variant, an intensity distribution function must be defined for the subsequent evaluation. In the exemplary embodiment, this intensity distribution function is stored in a lookup table and read out during the computer-aided evaluation.

Figure 6:
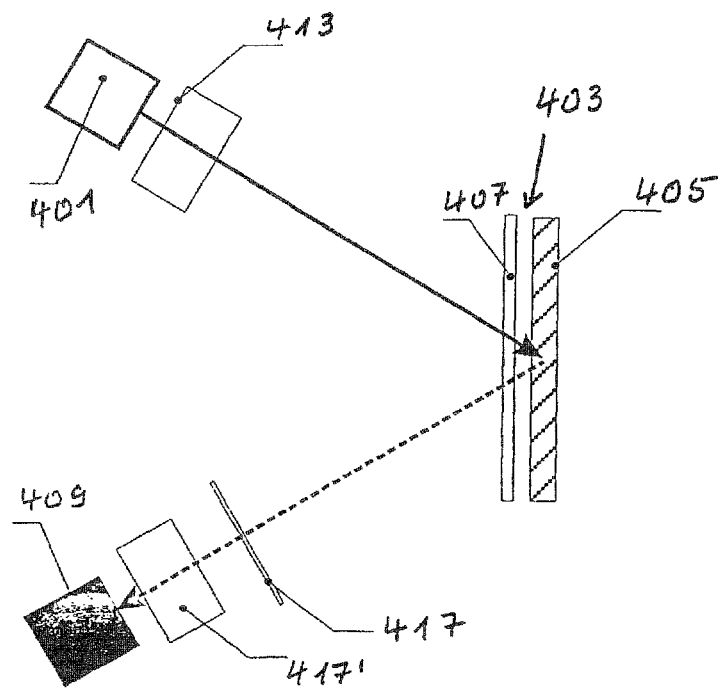
FIG. 6 a schematic diagram of an experimental setup according to the invention in one variant.

Another embodiment is illustrated in FIG. 6, wherein the elements of the measurement setup identical to those of FIG. 1 are indicated with identical reference symbols, augmented by 400.

The reference symbol 401 in FIG. 6 designates a broadband light source with a downstream wavelength filter 413. This wavelength filter can be used in two ways. On one hand, it can select the wavelengths desired for irradiating the sample 403 and thus limit the broadband spectrum of the light source 401, while simultaneously limiting the direction of the light.

The use of the wavelength filter 413 in this exemplary embodiment is therefore practical even when as an alternative to the broadband light source 403 a narrowband light source in form of the light emitting diode is used. It is particularly important for the evaluation technique on which the invention is based that the sample 403 is illuminated with light having a narrowband spectrum. In other words, the illumination light should neither have only a single wavelength, nor should the sample be illuminated sequentially with only a single wavelength. This principle fundamentally applies to all illustrated embodiments and variants and aids the skilled artisan with the selection to decide, if the wavelength filter 413 is or must be used only as direction-limiting filter, as wavelength-limiting filter or both based on a selected broadband or narrowband light source 403.

After the light has passed through the wavelength filter 413, it is incident on the sample 403 with the carrier 405 and the thin layer 407. That the carrier 405 is illustrated and used in form of an object slide should not be viewed as a limitation. The same exemplary embodiment can also be implemented with a micro-titer plate as carrier of the thin layer.

The thin layer 407 will now be discussed in more detail, because this layer can be additionally regarded to represent an integrated filter. In other words, the layer 407 is selected so as to have filter properties, because its reflectivity is wavelength-dependent.

The thus selectively reflected light is now transmitted towards the detector 409, after passing through a first detector filter 417 and a second detector filter 417'.

These detector filters 417, 417' can also have a direction-limiting function for improving the measurement result. With this measurement setup a signal can be measured at the detector 409 or the detector arrangement 409 which corresponds to the reflected radiation from the thin layer 407 and has an extremely favorable signal-to-noise ratio. The relative reflectivity of the thin layer, either across the entire area or in partial regions applied with the multi-spot method, can then be measured with extreme precision.

Figure 7:
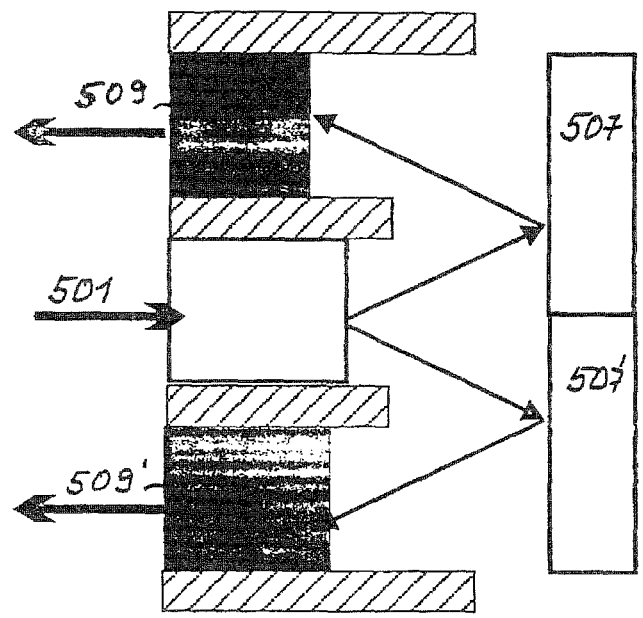
FIG. 7 a schematic diagram of a signal processing system according to the invention with the experimental setup according to FIG. 6.

The measurement setup according to the invention can be implemented in composite construction. This is schematically shown in FIG. 7. The respective reference symbols are once more augmented with respect to FIG., in this case by 500. The detector or the detector arrangement indicated in FIG. 7 with 509 detects the radiation reflected from the thin layer 507 or the partial regions of the thin layer 507. An additional detector 509' receives reference radiation. The reference radiation can be received, for example, from a region of the sample which is indicated here with 507' and is also irradiated. The region 507', however, was not pretreated so as to allow it to interact with the species of a sample to be identified, which would cause a change in the layer thickness.

The light source 501 is incident on both regions of the sample 507 and 507' in an identical fashion. Because this illustration is directed to explaining the possible composite construction of the measurement setup, the different filters and filter functions which cause an excellent signal-to-noise ratio in the measurement setup and which can be used either in combination or selectively severally, are not explained in more detail. Reference is hereby made to the previous exemplary embodiments.

If only a selection of filters or all aforementioned possible filters are employed in the measurement setup, or if for example the thin layer is selected to be selectively reflecting, so that it also operates as a filter, always depends on the species of a sample to be individually tested and can be easily decided by a skilled artisan.

Figure 8:
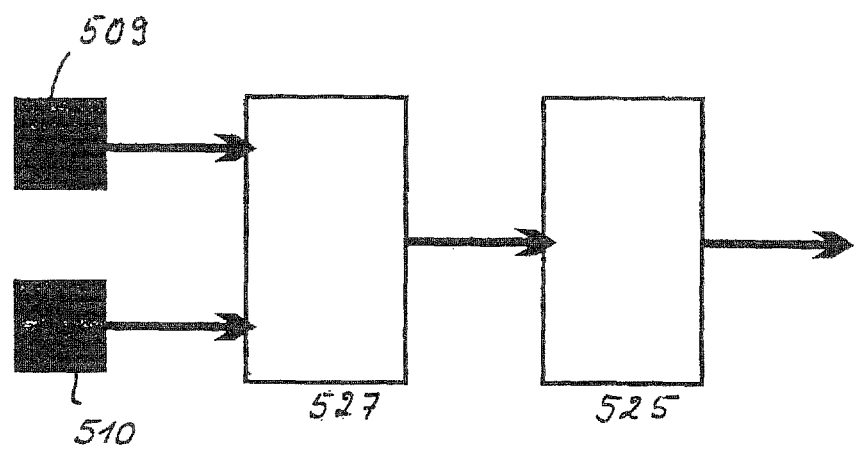
FIG. 8 a schematic diagram of an addition according to the invention of the signal processing system with the experimental setup according to FIGS. 6 and 7.

FIG. 8 shows an additional block diagram of a measurement setup according to the invention, which may be viewed as a possible extension of FIG. 7, namely when the reference region of the sample indicated in FIG. 7 with 507' which is responsible for the reference reflection and which transmits the reference reflection to the detector 509, is replaced by a reference sensor designated in FIG. 8 with 510, which is disposed at a different location of the measurement setup, in combination with a known defined distribution table of the incident light intensity in form of a lookup table stored in a computer, which is indicated in FIG. 8 with 525.

Because the two FIGS. 7 and 8 are related, the reference symbols in both Figures are identical as long as they designate identical elements.

In this exemplary embodiment, the detector 509 and the reference sensor 510 transmit the received signals to a comparator 527. The comparator operates to form the quotient of the respective signals received by the detector 509 and the reference sensor 510, i.e., from the reflected radiation at the sample 507 and the incident light radiation detected in the reference region 507'. The reflection coefficient formed in this way as the quotient is independent of the intensity of the incident light from the light source 501.

In an additional signal processing step, the spatial dependence must be taken into account with respect to the reference sensor 510, if the sensor 510 is not exactly positioned at the location of the measured sample 507. The aforementioned calibration table or lookup table 525 stored in a computer is used for this purpose.

It will be understood that this additional signal processing step may be omitted if the sensor 510 is positioned at the location of the measured sample 507.

Figure 9:
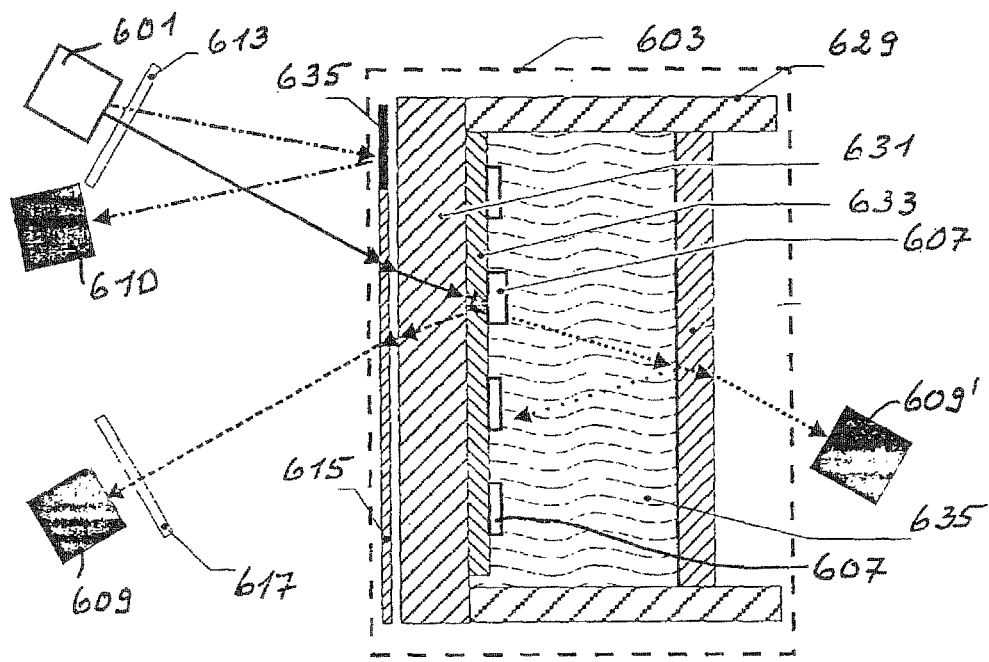
FIG. 9 a schematic diagram of an experimental setup according to the invention with a carrier in form of a micro-titer plate and the reflection at one spot.

With reference to FIG. 9, it should first be mentioned that the reference symbol 603 refers to a sample which includes a trough or a cavity of a micro-titer plate. This trough has a number of so-called spots which altogether form a several times interrupted thin layer 607 in form of a so-called patchy thin layer 607. The walls of the trough are designated with the reference symbol 629, whereas the bottom of the trough is designated with 631. This bottom 631 is initially prepared for receiving biomolecules and receptor molecules through activation and silanization, which is shown as bottom layer 633. These preparation steps have been described above and reference is made thereto. From the aforedescribed, it also becomes clear that the spots of the thin layer 607 have different affinities to different species of a sample to be tested. The illustrated trough contains a sample fluid with the species to be tested. These should then generate in interaction with the spots of the thin layer a detectable change in the layer thickness. For the purpose of the present invention, no specific difference is made between the sample representing the carrier of the thin layer exhibiting a change in the layer thickness and the sample with the species to be tested which cause the change in the layer thickness, because this is hereby immaterial; moreover, these concepts have been amply described, to which reference is made herein.

Light from a light source 601 is now incident on the sample 603 and passes initially the wavelength filter 613. An input filter in form of a spot filter 615 and one or several reflectors 635 are located on the side of the entering light. The one reflector shown in FIG. 9 operates to a direct the light incident from the light source 601 partially as reference beam onto the reference sensor 610. As seen from FIG. 9, the path of the incident light extends through the bottom plate 631 to the spots of the thin layer 607 where two superpositioned waves are created. The reflected superpositioned wave propagates towards the detector 609 and the transmitted superpositioned wave towards the additional detector 609'. It should also be mentioned that a detector filter 607 is also arranged in front of the detector 609.

Even if it were or should basically be possible that all listed filters 613, 615, 617 operate so as to be wavelength-limiting and/or direction-limiting and/or angle-limiting (collimating), the arrangement illustrated in FIG. 9 is designed so that additional collimating filters between the light source 601 and the spots of the thin layer 607 are not required.

Figure 10:
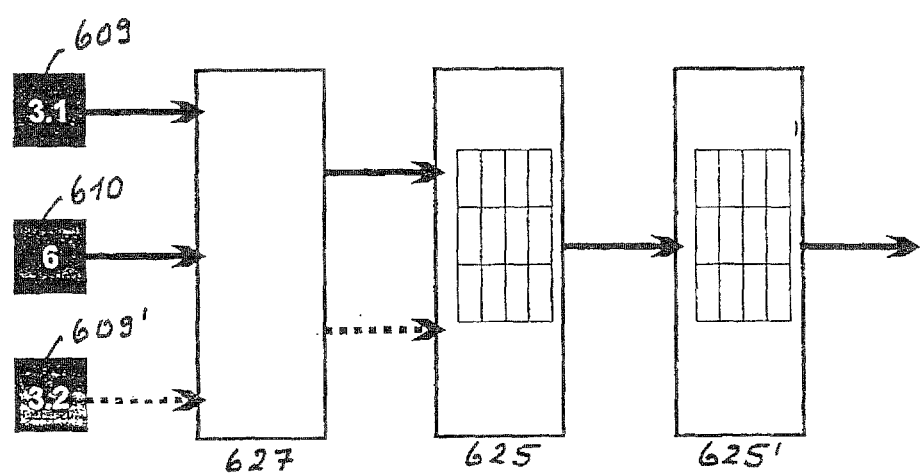
FIG. 10 a schematic diagram of a signal processing system according to the invention with the experimental setup according to FIG. 9 with additional use of comparators.

FIG. 10 shows a block circuit diagram which illustrates processing of the signals generated in the experimental setup of FIG. 9. As seen from FIG. 10, the input signals of the reflected superpositioned wave, as received by the detector 609, and the light directed by the reflector(s) 635 onto the reference sensor 610 as reference beam are supplied to a comparator 627. Optionally, the input signals of the transmitted superpositioned wave, as received from the additional detector 609', can also be supplied to the comparator 627.

The input signals of the transmitted superpositioned wave need not necessarily be evaluated. They may be disregarded. It has been observed in the course of many experiments that the signals of the transmitted superpositioned wave may not be measurable in the presence of absorbing fluids, as shown in the experimental setup of FIG. 9 and designated with 635.

The comparator 627 is constructed in two parts and forms, on one hand, the quotient of the signals received from the respective detector 609 and the reference sensor 610, i.e., from the reflected radiation on the sample 609 and the incident light radiation as detected in the reference region 610. On the other hand, the comparator 627 forms a quotient from the respective signals received from the detector 609' and the reference sensor 610, i.e., from the transmitted radiation and the incident light radiation as detected in the reference region 609'.

In this way, both the reflection and transmission coefficients can be formed. Both are as quotients independent of the intensity of the incident light from the light source 610. The discussion relating to the determination of the transmission coefficient is relevant only if the transmission coefficient can actually be measured.

It should also be mentioned in relation to the employed comparator 627 and to comparators in general that these are capable of operating fast with low energy consumption. Comparators are available both in digital technology, for comparing digital signals, as well as in analog circuit technology. Both types of comparators can here be used. Their respective application depends on the underlying measurement setup.

The previously obtained signals can then be converted directly, without additional computation, into an output signal by using the lookup tables 625, 625'. The respective processing units in form of the lookup tables 625, 625' stored in the computers can be implemented separately or combined with each other.

When in an additional signal processing step the spatial dependence with respect to the reference sensor 610 must additionally be taken into account, if the sensor 610 is not exactly positioned at the location of the measured samples 607, then this is also performed via a calibration table or lookup table which then replaces the lookup table 625, 625' stored in the computers, which is not separately shown in the block circuit diagram of FIG. 10.

The additional signal processing step is eliminated when the sensor 610 can be positioned at the location of the measured samples 607.

FIGS. 11a-11e show the changes imparted on a measured input signal by the signal processing according to the invention. For the purpose of illustration, reference is made here, if necessary, to the references symbols used in the previous exemplary embodiment, as primarily shown in FIG. 9. As can be seen, the described signal changes not only apply to the aforementioned exemplary embodiment, but are in general characteristic for the signal processing according to the invention within the context of the present application.

Figure 11A:
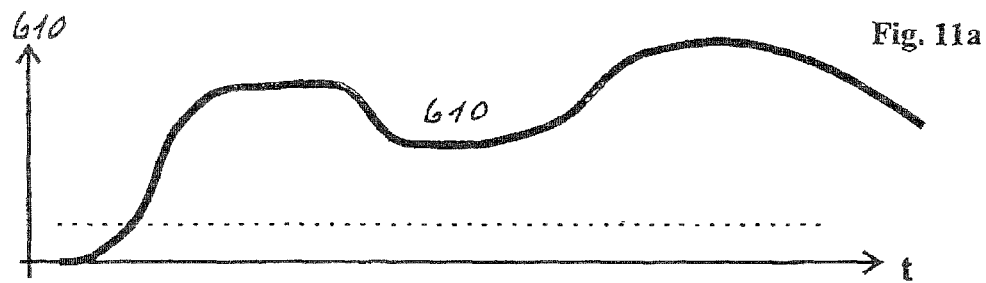
FIGS. 11a-e diagrams of measurement signals by using the measurement value processing according to the invention with formation of the reflection and transmission coefficients and further processing with comparators.

FIG. 11a shows the time dependence of the measured intensity of the light incident from the light source 601, as measured by the reference sensor 610.

Figure 11B:
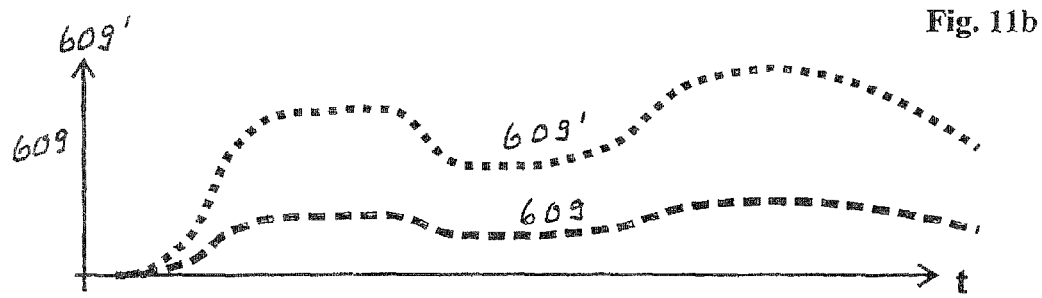

FIG. 11b shows the curve shape for the superpositioned field measured in reflection, starting at the detector and the detector arrangement 609, and for the superpositioned field measured in transmission, starting at the detector and the detector arrangement 609'.

This confirms the observation that the reflection is frequently weaker than the transmission. Both curve shapes vary proportional to the intensity of the incident light.

Figure 11C:
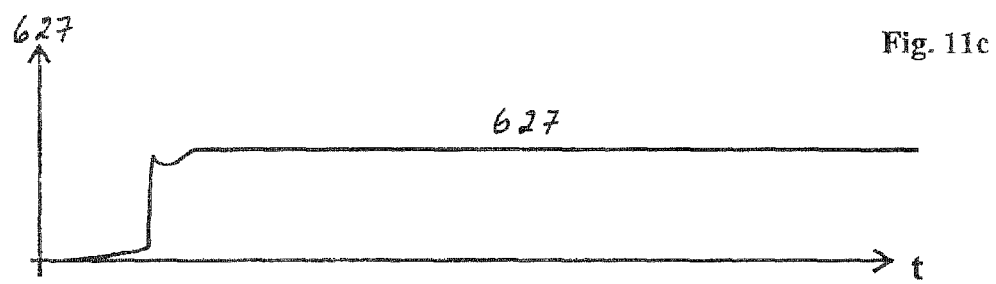

Accordingly, a true conclusion about the relative reflectivity is not possible by measuring the intensity alone. The same applies to transmission. The signal produced by the comparator 627 from the input values by forming the quotient of the respective signals received from the detector 609 and the reference sensor 610, i.e., from the radiation reflected on the sample 609 and the incident light radiation, as detected in the reference region 610, is shown in FIG. 11c. The thereby obtained relative signal is almost constant.

Figure 11D:
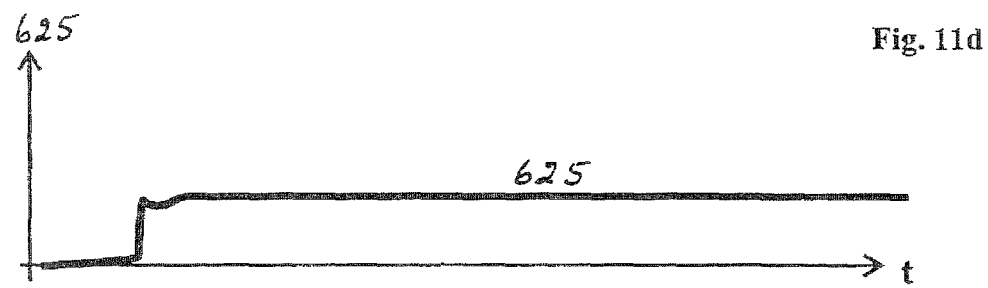

The additional signal processing step relates to forming a value for the thickness of the thin layer which changes due to interaction with species of the sample to be tested, or the partial regions of the thin layer in form of the spots 607. This signal processing step has been described above as the spatial dependence with reference to the reference sensor 510, 610, i.e., if the sensor 510, 610 is not exactly positioned at the location of the measured sample 507, 607. To this end, the aforedescribed calibration table or lookup table 525, 625 stored in a computer is used. The signal course resulting from the signal processing is illustrated in FIG. 11d.

Figure 11E:
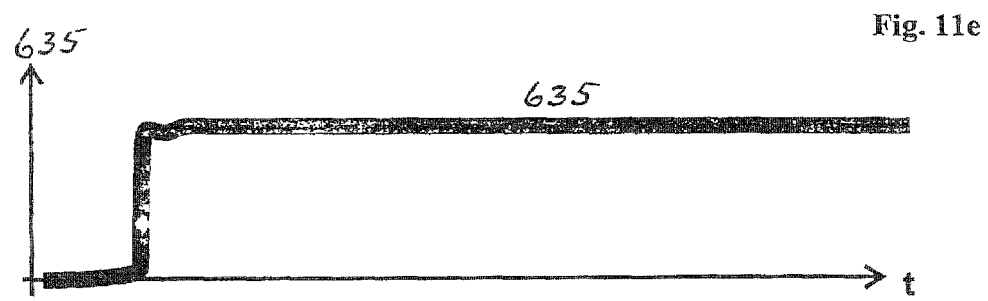

As the last signal processing step, shown in FIG. 11e, the effect of the fluid 635 and the species in the fluid to be analyzed must be taken into consideration. This is done by using the calibration table or lookup table 625' stored in a computer. The signal shape indicated with the reference symbol 635 correlates with the initial value 635 in FIG. 10 and represents the measurement result.

This measurement result is constant over a wide range of the incident light intensity, as long as the determined reflection coefficient is constant. The measurement value 635 is therefore obtained from the measurement of reflection and transmission on (as an example) the partial region of the thin layer 607 and the subsequent formation of the reflection and/or transmission coefficients without being affected by the intensity measured at the reference sensor 610.

In the following, several fundamental details applicable to the measurement setup according to the invention will be described. This is meant to provide clarity and to prevent repeating the details in view of the aforementioned exemplary embodiments.

The aforementioned exemplary embodiments demonstrated how the light reflected by the thin layer 7, 107, 207, 307, 407, 507 and 607 and/or the partial regions of the thin layer 7, 107, 207, 307, 407, 507 and 607 on the carrier 5, 105, 205, 305, 405, 505 and 605 is recorded via a suitable imaging optics with various, sometimes optional filters and filter functions by a detector or a detector arrangement 9, 109, 209, 309, 409, 509 and 609 and processed by the processing unit 11, always by specifically further processing the measured intensities and reference intensities. As shown with reference to FIG. 11, the evaluation became easier and its quality was significantly improved.

The layer thickness of the thin layer or the layer thickness of the partial region/spots of the thin layer, the change in thickness of which was actually observed and detected in this measurement, can be deduced from the reflection and/or transmission coefficients formed based on the measured intensities and reference intensities in a defined narrow wavelength range using the evaluation software.

For a faster quantitative determination with improved, simplified and faster determination, the determined intensity is according to the invention correlated with the corresponding optical layer thickness using a correlation function via, for example, the reflection coefficient in dependence of the employed narrow wavelength range of the LED or a broadband light source by using at least one corresponding filter, wherein the intensity can be obtained from a lookup table stored in a computer. This significantly reduces the complexity of the measurement and of the evaluation of the results while significantly increasing the demand for storage capacity in the evaluation unit 11, which does not pose a practical problem.

In the experimental setups illustrated in FIGS. 1-11, the carrier 5, 105, 205, 305, 405, 505 and 605 with the thin layer 7, 107, 207, 307, 407, 507 and 607 and/or the partial regions of the thin layer 7, 107, 207, 307, 407, 507 and 607 is irradiated approximately perpendicular. As an alternative, a different, slightly inclined angle of incidence of the light can be used. The measurements are generally performed in accordance with the basic principles of the reflectometric interference spectroscopy, which has been described repeatedly in the literature, but has not been adapted to practical applications.

Preferably, CCD cameras are used as detectors or sensors for the reflected light.

If a micro-titer plate is used instead of the carrier 5, 105, 205, 305, 405, 505 and 605 in form of an object slide, then several sensors can be provided for each well of the micro-titer plate for detection and data acquisition, in the exemplary embodiments and CCD sensors in form of one-dimensional arrays of CCD line sensors.

It is particularly important that these CCD sensors for each well capture the light radiation reflected by the receptor molecules interacting with the species to be analyzed due to changes in the layer thickness, as well as the underlying pattern of the respective well in form of the predetermined coding. With this type of detection, a high-quality temporal resolution of the changes in the layer thickness is attained.

For the practical implementation of the improved analysis of changes in the layer thickness of the thin layer or partial regions of the thin layer in form of spots according to the invention, it is initially quite important to quickly and unambiguously recognize the employed prepared carrier as a genuine product. Scannable barcodes are inadequate.

By employing the aforedescribed layer thickness analysis according to the invention through formation of reflection and transmission coefficients, with subsequent evaluation via the lookup tables, it has now become possible in combination with a pattern recognition described in other places to distinguish between a genuine product and a counterfeit product. This is a fundamental requirement for biomedical applications and/or applications in the field of homeland security.

For this reason, the pattern recognition in combination with the layer thickness analysis according to the invention on the basis of the respective pattern will now also be represented in the lookup table.

The Detection of the Layer Thickness Change in Combination with the Pattern Recognition Takes Place in the Following Variants:

The description of the variants is only exemplary and therefore relates to using a micro-titer plate with troughs, also referred to as cavities or wells. The bottom of these wells have not only the thin layer or partial regions of the thin layer, but are prepared for additional pattern recognition and include receptor molecules which interact with the species of a sample to be tested and which should cause a change in the layer thickness. This twofold preparation—pattern recognition and sample test—requires the presence of defined regions in the bottom of the wells 112, which during scanning of the bottoms of the wells do not produce any change or only an insignificant change in the measured intensities.

In the following regions, patterns can be applied and detected on the surface of the bottoms of the wells—and accordingly also on planar two-dimensional carriers, such as object slides:

patterns during activation of the bottoms of the wells and/or
patterns during surface treatment in form of a silanization and/or
patterns during the reaction with a biopolymer and/or
patterns during immobilization of the selected specific receptor molecules.

The subsequent measurement is therefore not only used to determine the change in the layer thickness due to interaction of the species to be tested in the sample with the thin layer, but also for the identification of the pattern previously applied on the thin layer, which represents a much more stringent requirement.

The aforementioned patterns are either applied by activating, for example silanizing, defined partial regions, or by reacting defined partial regions with the biopolymer, or by immobilizing the receptor molecules in defined partial regions, or by transferring the pattern structure to the next transformation step through pattern formation that had already occurred in a previous step.

For example, if already at the beginning only a defined partial region of the surface of the bottoms of the wells was activated, then only these activated regions can be silanized. The pattern therefore continues. Likewise, the patterns may be formed only during the conversion step of the silanization by applying a mask, by a specific multi-spot application and the like. The same applies to each of the conversion steps up to the immobilization of the receptor molecules.

The pattern formation described in this simplified manner is used for coding the respective micro-titer plate or likewise for coding of the respective planar carrier, for example for distinguishing counterfeit products from genuine products, thus providing quality assurance. It should be mentioned again that this pattern formation and coding as such are not part of the present invention. The present invention is directed to allow capturing, preferably automatically, and evaluating the formed pattern together with the change in the layer thickness caused by the respective observed interaction with high quality.

The light conducted to the bottoms of the wells and reflected at the surface of the thin layer distributed as multi-spots on the bottom of the wells is influenced in a completely different way. By the interaction of the sample to be tested with the receptor molecules which make up a portion of the regions of the thin layer distributed as multi-spots on the bottoms of the wells, the incident light is affected differently than, for example, in regions having no receptor molecules, because they are used for pattern recognition and quality assurance. The light reflected with different intensity, optionally also the light of the reference beam path, is subsequently detected by the detector arrangement which has at least one photo diode. The detector arrangement is again connected with an evaluation unit, as illustrated in conjunction with the above exemplary embodiments.

The reflected light is hereby detected by scanning from one well to the next well.

By using CCD technology, an individual well can be associated with the data acquisition in the respective evaluation unit. The number of scan and data acquisition processes corresponds exactly to the number of wells. The measurement values for the individual wells are time-sequentially captured.

Unlike in the conventional evaluation of data from reflectometric interference spectroscopy, it is now desirable to detect regions with high intensities and regions were almost nothing happens, i.e. where no intensity at all or only a very low intensity can be detected.

The detection method applying not only to a single well of a micro-titer plate, but instead to all wells, can then be simplified by providing a diode scanner line for each row of wells of a micro-titer plate. Because during an analysis the receptor molecules can be freely assigned in addition to the regions for the pattern recognition, the receptor molecules can be limited, for example, to one row of wells of the micro-titer plate or to defined rows. This significantly reduces the scanning and evaluation complexity and consequently also the required storage capacity in the evaluation unit. During scanning, a uniform signal stream is generated by the respective scanning CCD sensor, the CCD diode, which can be more easily processed by the evaluation unit.

This simplified embodiment has limits in the interactions between the receptor molecules and the species of a sample to be tested when the interactions are subject to a rapid kinetic process. Because a scan here includes scanning a complete row of wells, the scanning CCD sensor must be frequently and quickly moved back and forth, which may adversely affect the service life of the sensor.

It should be obvious to a person skilled in the art that all described embodiments can likewise be applied to thin layers on planar carriers, such as object slides, and micro-titer plates.

To increase the security of the evaluation process, the components required or optionally usable in the different embodiments, such as the light source, the various filters and sensors may also be provided with a specific coding. This measure enables calibration of the entire measurement setup, for example through matching with a lookup table, without significantly increasing the complexity. In this way, the initially measured intensity can be properly associated. For example, false amplitude values can thereby be effectively prevented.

What is claimed is:

1. A device for determining optical properties by measuring intensities on a thin layer, comprising:
    at least one light source constructed as a large-area light source and coupled with at least one wavelength filter for selecting a narrow-band wavelength range or a light source capable of emitting light in a narrow wavelength range,
    at least one first detector or sensor for a time-resolved measurement of the light incident from the at least one light source as reflected on a reference reflector,
    at least one second detector measuring the field of superposition in the said narrow wavelength range in reflection or in transmission,
    an evaluation unit that produces a relative signal by comparing input values received from the second detector and the first detector or sensor by forming the quotient of the said values, and by determining a measurement value based on the relative signal matched based on at least one stored lookup table.

2. The device of claim 1, wherein the light source comprises a high-power light emitting diode or a laser diode.

3. The device of claim 1, wherein the light source is implemented as a light source arrangement having several light sources.

4. The device of claim 3, wherein the several light sources comprise high-power light emitting diodes or laser diodes.

5. The device of claim 3, wherein the several light sources are arranged in form of a matrix or a ring.

6. The device of claim 1, further comprising an at least partially transparent carrier having the thin layer, said at least one light source being arranged separate from the carrier.

7. The device of claim 1, wherein the at least one first detector or the at least one second detector, or both, are constructed as a one-dimensional CCD sensor in form of a CCD array.

8. The device of claim 1, wherein the at least one first detector or the at least one second detector, or both, are constructed as a two-dimensional CCD sensor in form of a CCD image sensor.

9. The device of claim 6, wherein the carrier is a planar, two-dimensional carrier.

10. The device of claim 6, wherein the carrier is a micro-titer plate.

11. The device of claim 6,
wherein the thin layer is divided into several coated partial regions (multi-spots) arranged on the at least partially transparent carrier,
wherein the at least one light source irradiates a corresponding coated partial region having at least two boundary surfaces with superimposed wave fields producing at least one superpositioned wave, and
wherein superpositioned wave fields produce a superpositioned field configured to be transmitted to the at least one detector,
the device further comprising at least one intensity sensor being associated with at least a portion of the partial regions for determining the intensity of the light locally incident on the coated partial region.

12. The device of claim 1, wherein a spectral half width of the narrow wavelength range is 20-35 nm.

13. The device of claim 1, wherein the narrow wavelength is a wavelength of a narrowband light emitting diode.

* * * * *